(12) United States Patent
Tan et al.

(10) Patent No.: US 8,389,619 B1
(45) Date of Patent: *Mar. 5, 2013

(54) IN-SITU NANOCOMPOSITES FROM POLYMERIZATION OF AN ARYLOXYBENZOIC ACID IN THE PRESENCE OF DETONATION NANODIAMOND

(75) Inventors: Loon-Seng Tan, Centerville, OH (US); David H. Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 622 days.

This patent is subject to a terminal disclaimer.

(21) Appl. No.: 12/322,955

(22) Filed: Feb. 5, 2009

Related U.S. Application Data

(60) Provisional application No. 61/070,596, filed on Feb. 21, 2008.

(51) Int. Cl.
*C08K 3/04* (2006.01)
(52) U.S. Cl. ........ 524/496; 524/495; 524/874; 977/734; 977/737; 977/740; 977/753
(58) Field of Classification Search .................. 524/495, 524/496, 874; 977/734, 737, 740, 753
See application file for complete search history.

(56) References Cited

U.S. PATENT DOCUMENTS

| | | | | |
|---|---|---|---|---|
| 7,732,642 B1 * | 6/2010 | Tan et al. | ....................... | 568/319 |
| 7,771,696 B2 * | 8/2010 | Wang et al. | ................ | 423/447.1 |
| 7,960,471 B1 * | 6/2011 | Tan et al. | ....................... | 524/877 |
| 2006/0121279 A1 * | 6/2006 | Petrik | ............................ | 428/403 |

OTHER PUBLICATIONS

Choi, Ja-Young, Se-Jin Oh, Hwa-Jeong Lee, David H. Wang, Loon-Seng Tan, and Jong-Beom Baek. (May 25, 2007) "In-Situ Grafting of Hyperbranched Poly(ether ketone)s onto Multiwalled Carbon Nanotubes via the A3+B2 Approach." Macromolecules, 40, pp. 4474-4480.*

Wang, David H., Loon-Seng Tan, Houjin Huang, Liming Dai, and Eiji Osawa. (Dec. 9, 2008) "In-Situ Nanocomposite Synthesis: Arylcarbonation and Grafting of Primary Diamond Nanoparticles with a Poly(ether-ketone) in Polyphosphoric Acid." Macromolecules, 42, pp. 114-124.*
Wang, David H., Peter Mirau, Bing Li, Christopher Y Li, Jong-Beom Baek, and Loon-Seng Tan. (Jan. 17, 2008) "Solubilization of Carbon Nanofibers with Covalently Attached Hyperbranched Poly(ether-ketone)." Chemical Materials, 20, pp. 1502-1515.*
Baek, Jong-Beom, Christopher B. Lyons, and Loon-Seng Tan. (Sep. 3, 2004) "Grafting of Vapor-Grown Carbon Nanofibers via in-Situ Polycondensation of 3-Phenoxybenzoic Acid in Poly(Phosphoric acid)." Macromolecules, 37, pp. 8278-8285.*
Wang, David H., Loon-Seng Tan, Houjin Huang, Liming Dai, and Eiji Osawa. (Mar. 27, 2007) "Grafting of Detonation Nanodiamond with m-poly(etherketone) in polyphosphoric acid." ACS National Meeting. *Not attached as it is provided in its entirety in paragraph 1 of the Office Action.*

* cited by examiner

*Primary Examiner* — Ling Choi
*Assistant Examiner* — Darcy D LaClair Lynx
(74) *Attorney, Agent, or Firm* — Bart S. Hersko; AFMCLO/JAZ

(57) ABSTRACT

A poly(ether-ketone) composite of the formula:

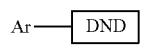

wherein DND is detonation nanodiamond particle; wherein Ar represents ether-ketone repeating groups of the formula

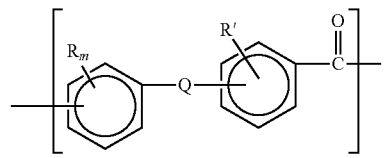

wherein Q is —O— or —O—$(CH_2)_n$—O—, wherein n has a value of 2-12; wherein R is —H, —$CH_3$, or —$C_2H_5$, m has a value of 1 or 2; wherein R' is —H or —$CH_3$; and wherein — denotes the presence of a direct C—C bond between Ar and DND. Also provided is a process for preparing the nanocomposites.

3 Claims, No Drawings

IN-SITU NANOCOMPOSITES FROM POLYMERIZATION OF AN ARYLOXYBENZOIC ACID IN THE PRESENCE OF DETONATION NANODIAMOND

CROSS REFERENCE TO RELATED APPLICATION

This application claims priority of the filing date of Provisional Application Ser. No. 61/070,596 filed Feb. 21, 2008.

RIGHTS OF THE GOVERNMENT

The invention described herein may be manufactured and used by or for the Government of the United States for all governmental purposes without the payment of any royalty.

BACKGROUND OF THE INVENTION

The present invention relates to compositions of matter for thermoplastic nanocomposites containing nanodiamond particulates known commonly as detonation nanodiamond.

Although detonation nanodiamond (DND) was discovered relatively early (in the 1960's) in USSR as compared to other carbon nanoparticles, viz. fullerenes, single-walled, double-walled, multi-walled carbon nanotubes (SWNT, DWNT and MWNT) and nanofiber (CNF), DND has received little or no attention until 1988 when two landmark papers appeared in open literature. Detonation nanodiamond was so-named because of its production by detonation of 2,4,6-trinitrotoluene (TNT)/1,3,5-trinitro-triazacyclohexane (hexogen) explosives in a closed steel chamber either in gaseous atmosphere, e.g. $CO_2$ (dry method) or in water (wet method). DND is also known by two other common names, viz. ultra-dispersed diamond (UDD) and ultrananocrystalline diamond (UNCD) particulates, because the basic constituents (primary particles) have the characteristic size in the range of 2-10 nm (ave. diameter ~4-5 nm) and very large specific surface area (>>200 $m^2/g$). With the important advantages such as availability in larger quantities (industrial production capabilities existing in Russia, Ukraine, China and Belarus) and at moderate cost, DND is very attractive as a material platform for nanotechnology. Furthermore, DND has been shown to be non-cytotoxic and biocompatible. These features give DND an additional appeal to bio-related applications in view of its rich surface chemistry that could be modified with relative ease. The surface functional groups identified by various spectroscopic techniques are mostly oxygenated moieties such as —$CO_2H$ (carboxylic acid), lactone, C=O (keto carbonyl), —C—O—C (ether) and —OH (hydroxyl). In addition, inter-particle hydrogen-bonding and formation of ester, ether, and anhydride bonds are believed to play important roles in assembling the DND primary particles into much larger aggregates with sizes ranging from a few hundred nanometers ("core agglutinates") to a few ten microns ("agglomerates"). In fact, under appropriate pH conditions, these inter-particle binding forces are believed to be responsible for the large-scale self-assembly of acid-treated DND into fibers and thin films from drying the suspension. Further, the primary particles in the core agglutinates are so strongly bound together that the total binding force is even greater than that in SWNT ropes, which stems from noncovalent (van deer Waals and π-π) interactions between individual nanotubes. Indeed, it is known that even powerful ultrasonication of crude nanodiamond aggregates could only produce core agglutinates with average size of 120 nm.

Covalent surface modifications of diamond nanoparticles are generally focused on improving the DND processability and introducing suitable functional groups to impart, enhance or tailor certain properties, and eventually, to increase system compatibility and performance. The synthetic tools for such modification have entailed the conversion of the oxygenated groups (i.e. carboxylic acid, hydroxyl etc.) to suitable functionalities for subsequent manipulation. For example, DND was fluorinated using a $F_2/H_2$ mixture to afford 8.6 atom % fluorine (replacing OH, $CO_2H$ etc.) on the surface, and the fluorinated DND was then used as a precursor for the preparation of alkyl-, amino-, and acid-functionalized DNDs that showed an increased solubility in polar solvents and much smaller size in nanoparticle agglomeration, or coated covalently onto an amine-functionalized glass surface. High temperature (400-850° C.) treatment of DND powders in the presence of $H_2$, $Cl_2$ or $NH_3$ has also led to converting the surface carboxylic acid to alcohol, acid chloride, and nitrile, in that order. More recently, the reduction of the surface —$CO_2H$ by $BH_3$.THF complex to the corresponding —$CH_2OH$, followed by O-silylation with (3-aminopropyl) trimethoxysilane and coupling with biotin or a short peptide to generate promising bio-nano hybrid materials has been reported.

Besides the aforementioned reports on the covalent functionalization of DND surfaces that were likely to have occurred at the outermost layer with mixed $sp^2$ and $sp^3$ carbons, Li et al. (Li, L.; Davidson, J. L.; Lukehart, C. M. *Carbon* 2006, 44, 2308) reported the first example of DND-polymer nanocomposites, in which poly(methyl methacrylate) brushes were grafted from initiators, previously and covalently bonded on the DND surface, by atom transfer radical polymerization (ATRP) process. Most recently, Zhang et al. (Zhang, Q.; Natio, K.; Tanaka, Y.; Kagawa, Y. *Macromolecules* 2008, 41, 536) reported the grafting of aromatic polyimides from nanodiamonds. In these reports, the DND component in the polymer nanocomposites was actually aggregates (20-50 nm) of primary particles, resulting in polymer-DND particles with sizes 100-200 nm.

Conceptually, there are three general techniques for dispersing chemically unmodified DND in the linear polymer matrices: (1) melt blending (2) solution blending, and (3) reaction blending. For the reaction blending route, there are two scenarios: (a) in-situ polymerization of monomers (AB) or co-monomers (AA+BB) in the presence of dispersed DND that occurs without forming any covalent bonding between the DND and the matrix polymer, or (b) in-situ grafting of AB monomers that occurs with direct covalent bonds formed between the DND and the matrix polymer. Thus, using Friedel-Crafts acylation as a synthetic tool to exemplify reaction blending route to DND-based nanocomposites, it is shown here how to chemically attach meta-poly(ether-ketone) onto the surfaces of DND via in-situ polymerization of an appropriate AB monomer such as m-phenoxybenzoic acid in the presence of DND in poly(phosphoric acid).

Accordingly, it is an object of the present invention to provide a process for attaching a poly(ether-ketone) onto the surfaces of diamond nanoparticles.

It is another object of this invention to provide polymer-grafted nanodiamonds particles and associated nanocomposites.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided a poly(ether-ketone) composite of the formula:

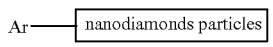

wherein Ar represents ether-ketone repeating groups of the formula

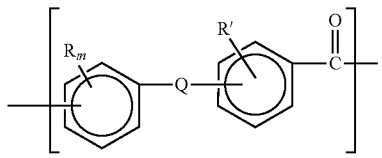

wherein Q is —O— or —O—$(CH_2)_n$—O—, wherein n has a value of 2-12; wherein R is —H, —$CH_3$, or —$C_2H_5$, m has a value of 1 or 2; wherein R' is —H or —$CH_3$; and wherein — denotes a direct C—C bond between Ar and carbon nanofibers or multi-walled carbon nanotubes. Preferably, Q is —O—, R is —H, m is 2 and R' is —H. Nanodiamond particles include primary particles (3-5 nm) and agglutinates (10-150 nm).

Also provided is a process for preparing the above nanocomposites.

DETAILED DESCRIPTION OF THE INVENTION

The composite of this invention is prepared by reacting an aromatic acid of the formula

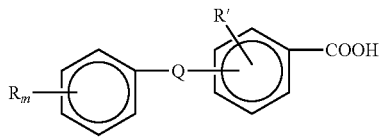

wherein R, R', m and Q are as described above, with detonation nanodiamond particulates in polyphosphoric acid (PPA), as described below.

Suitable aromatic acids useful in this reaction include 3-phenoxybenzoic acid, 4-phenoxybenzoic acid, 3-(2,6-dimethylphenoxy)benzoic acid, 3-phenoxy-2-methylbenzoic acid, and the like.

Attachment of the poly(ether-ketone) onto the surfaces of nanodiamond particulates is conducted in polyphosphoric acid (PPA). Preliminarily it is helpful to describe the chemistry of phosphoric acids and strong phosphoric acids or polyphosphoric acids as follows: As used herein the term "phosphoric acid(s)" means commercial phosphoric acid(s) containing 85-86% $H_3PO_4$. The strong phosphoric acids, or polyphosphoric acids referred to as PPA (polyphosphoric acid) are members of a continuous series of amorphous condensed phosphoric acid mixtures given by the formula $H_{n+2}P_nO_{3n+1}$ or HO—$(PO_3H)_n$—H where the value of n depends on the molar ratio of water to phosphorus pentoxide present.

In its most general definition, polyphosphoric acid composition can range from distributions where the average value of n is less than unity, giving rise to a mobile liquid, to high values of n, where the polyphosphoric acid is a glass at normal temperatures. Because the species of polyphosphoric acid are in a mobile equilibrium, a given equilibrium composition can be prepared in many ways. For instance, the same distribution or polyphosphoric acid composition could be prepared by either starting with concentrated orthophosphoric acid ($H_3PO_4$, n=1) and driving off water or by starting with phosphorus pentoxide ($P_2O_5$) and adding an appropriate amount of water.

All polyphosphoric acid compositions can be described as a ratio of $P_2O_5$ and water by reducing the various species present (on paper) to $P_2O_5$ and water. We will then use the convention that polyphosphoric acid composition will be expressed in terms of a $P_2O_5$ content (as a percentage) defined as $P_2O_5$ content =(weight of $P_2O_5$)/(weight of $P_2O_5$+weight of water)×100.

Thus, the $P_2O_5$ content of pure orthophosphoric acid could be derived by reducing one mole of $H_3Pa_4$ to 0.5 moles $P_2O_5$+1.5 moles $H_2O$. Converting to weights gives the $P_2O_5$ content as (0.5*142)/((0.5*142)+(1.5*18.01))*100%=72.4%

Similarly, the $P_2O_5$ content of commercial polyphosphoric acid can be derived in the following way. Polyphosphoric acid is available commercially in two grades, 105% and 115%. These percentages refer to $H_3PO_4$ content, which means that 100 g of the two grades contain 105 and 115 grams of $H_3PO_4$. The $P_2O_5$ content of 115% polyphosphoric acid can then be calculated knowing the $P_2O_5$ content of 100% $H_3PO_4$:

(115 g/100g)*72.4%=83.3%

The polymerization is conducted in polyphosphoric acid (PPA) at a polymer concentration of about 5 weight percent at a temperature of about 130° C. The acid, detonation nanodiamond particulates, and PPA (83% assay) are combined and stirred with dried nitrogen purging at about 130° C. for about 3 hours. Additional $P_2O_5$ is then added in one portion; and heating is continued, with stirring for about 24-60 hours. The reaction product is then precipitated from the PPA reaction solution with water or other polymer nonsolvent. The amount of $P_2O_5$ added is optimized at 25 wt % of the PPA used at the beginning of the reaction, leading to a total $P_2O_5$ content of about 86.7%.

The following examples illustrate the invention:

Example 1

Functionalization of DND with
4-(2,4,6-trimethylphenoxy)benzoic acid
(TMPB-g-DND)

Into a 100 mL resin flask equipped with a high torque mechanical stirrer, and adaptors for nitrogen inlet and outlet, 4-(2,4,6-trimethylphenoxy)benzoic acid or TMPBA (0.20 g, 0.78 mmol), DND (0.20 g), PPA (83% $P_2O_5$ assay, 10 g) and phosphorus pentoxide ($P_2O_5$, 2.5 g) were charged, and the reaction mixture was stirred under dried nitrogen purging at 130° C. for 72 h. After cooling down to room temperature, water was added to the reaction mixture. The resulting precipitate was collected, washed with diluted ammonium hydroxide and Soxhlet extracted with water for three days and methanol for three days. It was then dried over $P_2O_5$ under reduced pressure at 100° C. for 72 h to afford 0.31 g (80% yield) of gray solid. Anal. Calcd. for $C_{7.89}H_3N_{1.75}O_{0.56}$ (based on the assumption that for every 100 carbon, there are 2.35 4-(2,4,6-trimethylphenoxy)benzoyl groups attached): C, 87.58%; H, 2.10%; N, 1.75%; O, 7.01%. Found: C, 86.73%; H, 1.58%; N, 1.90%; O, 7.51%. $^1$H-NMR (DMSO-$d_6$, δ in ppm): 2.03 (s, 6H), 2.27 (s, 3H), 6.88 (d, 2H), 7.001 (s, 2H), 7.69 (d, 2H). FT-IR (KBr, cm$^{-1}$): 3418 (OH), 2922 (CH$_3$), 1712 (O—C=O), 1658 (C—C=O), 1595, 1234, 1157, 1079.

Example 2

PPA-Treated DND

In order to investigate the effect of PPA/$P_2O_5$ on DND, a control experiment was conducted, in which DND (0.20 g), alone was heated in PPA/$P_2O_5$ [83% $P_2O_5$ assay, 20 g) and phosphorus pentoxide ($P_2O_5$, 5.0 g] at 130° C. for three days to afford a sample (0.18 g), designated as PT-DND, in 90% recovery yield. The work-up procedure was same as that for Example 1.

The IR spectrum of PT-DND is essentially identical with that of the pristine DND except that most of the absorption peaks of PT-DND are sharper. The TGA results indicate that the thermo-oxidative stability of PT-DND has been significantly improved over the pristine DND. The powder samples PT-DND shows a 5% weight loss at 577° C., 50° C. higher than the pristine DND, in air. PT-DND was also observed to generate a higher char yield (94.5%) than the pristine DND (92.4%) in nitrogen (Table 2). The higher stability of PT-DND is probably due to the removal of some inorganic impurities from the pristine DND during PPA treatment. Scanning electronic microscopy (SEM) results indicated that the sizes and shapes of PT-DND are similar to the ground pristine DND, albeit the surface of PT-DND has become slightly smoother. All above results indicate that apart from being an efficient Friedel-Crafts catalyst, PPA is also chemically benign to the DND structure, and improves the thermal stability of DND by effectively removing the residual contaminants.

Example 3

Representative Procedure for Preparation of In-Situ Nanocomposites (mPEK with 20 wt % DND Load)

Into a 250 mL resin flask equipped with a high-torque mechanical stirrer, adaptors for nitrogen inlet/outlet, and a solid-addition port, 3-phenoxybenzoic acid (PBA; 4.00 g, 18.7 mmol), DND (1.00 g), and PPA (83% $P_2O_5$ assay; 100 g) were added, and the reaction mixture was stirred under dry nitrogen purge at 130° C. for 3 h. $P_2O_5$ (25.0 g) was then added in one portion via the solid-addition port. The initially dark mixture (due to dispersion of DND) became lighter and more viscous as the polymerization of PBA and the growth of mPEK grafts on progressed. The temperature was maintained at 130° C. for 48 h. At the end of the reaction, the color of mixture was dark brown, and water was added to the reaction vessel. The resulting purple nanocomposite clusters were put into a Waring blender, and the solid chunks were chopped, collected by suction filtration, and washed with diluted ammonium hydroxide. Then, the nanocomposite product was then Soxhlet-extracted with water for 3 days and then with methanol for 3 more days and was finally dried over phosphorus pentoxide under reduced pressure at 100° C. for 72 h to give a purple powder in quantitative yield. Anal. Calcd for $C_{6.84}H_{3.44}N_{0.03}O_{0.44}$: C, 82.20%; H, 3.44%; N, 0.44%; O, 13.92%. Found: C, 81.44%; H, 3.57%; N, 0.21%; O, 12.74%. FT-IR (KBr; cm$^{-1}$): 3431, 3063, 1657 (carbonyl), 1576, 1433, 1237, 1161, 877, 757.

Example 4

Extraction of Free mPEK from 20 wt % mPEK-g-DND

Although the AB-monomer (3-phenoxybenzoic acid) is soluble in hot methanol, mPEK is insoluble in hot methanol, but it is very soluble in methylene chloride (CH$_2$Cl$_2$). Therefore, 20 wt % mPEK-g-DND (purple powder sample, 1.00 g) was dispersed in CH$_2$Cl$_2$ in a closed vial at room temperature for 48 h. During this period, the suspension was sonicated, and then filtered through 0.2 μm PTFE membrane. The purple solid was collected. It was dispersed in fresh CH$_2$Cl$_2$, sonicated and filtered again. The filtrate was spotted on a thin-layer chromatography (TLC) plate, which was checked for fluorescence due to mPEK with a hand-held UV lamp. The above extraction routine was repeated 3 times until TLC showed no sign (fluorescent spot) of free mPEK in the CH$_2$Cl$_2$ filtrate. After the removal of CH$_2$Cl$_2$ from the sample, the residue was dried in vacuum to afford 0.92 g of purple powder. This test indicates that most of mPEK was grafted onto DND.

Example 5

Various polymerizations were carried out with different ratios of the AB-monomer, 3-phenoxybenzoic acid (PBA) and DND using the procedure given in Example 1. The elemental analysis results of these nanocomposites as well as those for pristine DND TMPB-g-DND and PT-DND (for reference and comparison purposes) are given in Table 1:

TABLE 1

Element analysis data for pristine, TMPB-g-DND, and PT-g-DND and mPEK-g-DND.

| Sample | Elemental Analysis | C (%) | H (%) | N (%) | O (%) |
|---|---|---|---|---|---|
| Pristine DND | Calcd | 100 | 0 | 0 | 0 |
| | Found[a] | 90.35 | 1.06 | 2.06 | 4.87 |
| TMPB-g-DND | Calcd[b] | 87.58 | 2.10 | 1.75 | 7.01 |
| | Found | 86.73 | 1.58 | 1.90 | 7.51 |
| PT-DND | Calcd | 100 | 0 | 0 | 0 |
| | Found | 90.87 | 1.10 | 1.92 | 4.98 |
| mPEK-g-DND, 1 wt % | Calcd[c] | 79.74 | 4.05 | 0.02 | 16.19 |
| | Found | 79.43 | 4.33 | <0.1 | 15.87 |
| mPEK-g-DND, 2 wt % | Calcd[c] | 79.82 | 4.01 | 0.04 | 16.06 |
| | Found | 79.18 | 4.21 | <0.1 | 15.67 |
| mPEK-g-DND, 5 wt % | Calcd[c] | 80.25 | 3.92 | 0.11 | 15.71 |
| | Found | 80.07 | 3.92 | 0.08 | 15.67 |
| mPEK-g-DND, 10 wt % | Calcd[c] | 80.41 | 4.26 | 0.21 | 15.12 |
| | Found | 80.69 | 3.84 | 0.16 | 14.93 |
| mPEK-g-DND, 20 wt % | Calcd[c] | 82.20 | 3.44 | 0.44 | 13.92 |
| | Found | 81.44 | 3.57 | 0.21 | 12.74 |
| mPEK-g-DND, 30 wt % | Calcd[c] | 83.47 | 3.14 | 0.66 | 12.73 |
| | Found | 83.53 | 3.14 | 0.61 | 12.48 |

[a]Based on the elemental analysis result, the empirical formula of pristine DND is $C_{7.52}H_{1.06}N_{0.15}O_{0.30}$, which was used in the subsequent calculation of mPEK-g-DND nanocomposites compositions.
[b]Its molecular formula of $C_{7.89}H_3N_{1.75}O_{0.56}$ is based on the assumption that for every 100 carbon, there are 2.35 2,4,6-trimethylphenoxybenzoyl groups attached. The molecular formula of 4-(2,4,6-trimethylphenoxy)benzoyl group is $C_{16}H_{15}O_2$.
[c]Calculated composition based on the assumption that the molar mass of the repeat unit of mPEK ($C_{13}H_8O_2$) is 196.20. Empirical formulas derived from the molar ratios of DND: mPEK, i.e., C: $C_{13}H_8O_2$, are as follows: (1/99) $C_{6.64}H_{4.05}N_{0.0016}O_{1.01}$; (2/98) $C_{6.65}H_{4.01}N_{0.003}O_{1.00}$; (5/95) $C_{6.67}H_{3.92}N_{0.008}O_{0.98}$; (10/90) $C_{6.70}H_{4.22}N_{0.015}O_{0.95}$; (20/80) $C_{6.84}H_{3.44}N_{0.03}O_{0.44}$; (30/70) $C_{6.91}H_{3.12}N_{0.05}O_{0.79}$.

Example 6

The glass-transition temperatures ($T_g$'s) and exotherms of mPEK-g-DND samples were determined by DSC. The powder samples were heated to 300° C. in the DSC chamber in the first run and cooled to ambient temperature at 10° C./min under nitrogen purge. Then, the samples were heated to 300° C. at 10° C./min in the second run. As shown in data summarized in Table 2, pure mPEK displays a $T_g$ at 136° C. during both first and second heating runs. However, the mPEK-g-DND samples show exotherms with peak values varying between 131 and 147° C., and no $T_g$'s were detected during the first heating runs. The exothermic peak value increases somewhat proportionately with DND contents. The exotherms of as-produced samples (i.e. without prior heat treatment to 300° C.) were attributed to the storage strain energy induced by the shear field (i.e. generated by mechanically stirring) during the polymerization process at 130° C. in viscous PPA. After polymerization, the samples were cooled down and the storage strain energy of mPEK was retained kinetically by the increase in PPA bulk viscosity. When they were heated close to $T_g$'s, the frozen polymer chains started to move, with the strain energy being released. For neat mPEK, no exotherm was observed during the first heating run. Since its $T_g$ at 136° C. is very close to polymerization temperature (130° C.), either the storage strain energy did not build up or it was released just before cooling down due to its lower viscosity than mPEK-g-DND after polymerization. The $T_g$'s of nanocomposites appear in the second heating scan. As the amount of DND increased, the $T_g$'s of the nanocomposites gradually increased to 155° C. for 30 wt %. This is consistent with the rationale that the attachment of flexible mPEK chains to the rigid DND surface imposes constraints over their mobility, resulting in as much as a 19° C. increase in the glass-transition temperature. Most importantly, the presence of a single $T_g$ for all the mPEK-g-DND samples provide a strong support to the assertion that the polymer-grafted diamond nanoparticles were indeed homogeneously dispersed throughout the nanocomposites, and the effectiveness of our in-situ polymerization method.

TABLE 2

Physical properties of mPEK-g-DND composites.

| | | DSC | | | TGA | | | |
| | | 1st Heating | | 2nd Heating | in nitrogen | | in air | |
| DND (wt %) | $[\eta]^a$ (dL/g) | $T_{exo}^b$ (° C.) | ΔH (J/g) | $T_g^c$ (° C.) | $T_{d5\%}^d$ (° C.) | Char$^e$ (%) | $T_{d5\%}^d$ (° C.) | Char$^e$ (%) |
|---|---|---|---|---|---|---|---|---|
| 0 | 0.46 | 136 ($T_g$) | — | 136 | 402 | 47.1 | 414 | 0.80 |
| 1.0 | 0.67 | 131 | 2.64 | 138 | 461 | 46.8 | 448 | 1.18 |
| 2.0 | 0.88 | 132 | 3.78 | 138 | 478 | 49.0 | 452 | 1.56 |
| 5.0 | 1.03 | 134 | 6.3 | 139 | 467 | 50.3 | 463 | 1.56 |
| 10 | 1.42 | 137 | 7.8 | 143 | 501 | 54.1 | 489 | 1.78 |
| 20 | 1.37 | 143 | 6.5 | 151 | 488 | 58.6 | 498 | 1.14 |
| 30 | 0.95 | 147 | 5.9 | 154 | 510 | 62.5 | 502 | 0.42 |

$^a$Intrinsic viscosity measured in MSA at 30.0 ± 0.1° C.
$^b$Exothermic peak on DSC thermogram obtained in $N_2$ with a heating rate of 10° C./min.
$^c$Inflection in baseline on DSC thermogram obtained in $N_2$ with a heating rate of 10° C./min.
$^d$Temperature at which 5% weight loss recorded on TGA thermogram obtained with a heating rate of 10° C./min.
$^e$Char yield at 850° C.

Example 7

Degree of Polymerization (DP) for the mPEK Grafts

On the basis of the experimental results in our model compound study (Example 1), it is proposed that with an appropriate ether-activated, aromatic carboxylic acid, functionalization of DND via Friedel-Crafts acylation in PPA:$P_2O_5$ (w/w 4:1) medium could result in arylcarbonylation of 2.35 carbons in every 100 carbon sites. Furthermore, the arylcarbonylation reaction is most likely to occur at the $sp^2C$—H defect sites. On this assumption, it is determined the upper-limit values for the DP and molecular weight of each DND-bound mPEK, ranging from a DP of 5.6 with the corresponding MW of 1,099 Da to a DP of 233 and MW of 45,715 Da. Our computation algorithm and results are shown in Table 3.

TABLE 3

Calculation of Total Number of Grafting Sites and Degree of Polymerization (DP) for mPEK-g-DND Samples

| Sample | wt % (DND/PBA) | wt % (DND/mPEK)$^a$ | mol DND$^b$ | mol mPEK$^b$ | mol grafting site$^c$ | mPEK DP/chain$^d$ | mPEK MW/chain$^e$ |
|---|---|---|---|---|---|---|---|
| mPEK-g-DND, 1 wt % | 1/99 | 1.1/98.9 | 0.092 | 0.504 | 0.00216 | 233 | 45715 |
| mPEK-g-DND, 2 wt % | 2/98 | 2.2/97.8 | 0.183 | 0.498 | 0.00430 | 116 | 22759 |
| mPEK-g-DND, 5 wt % | 5/95 | 5.4/94.6 | 0.450 | 0.482 | 0.01058 | 45.6 | 8947 |
| mPEK-g-DND, 10 wt % | 10/90 | 10.8/89.2 | 0.899 | 0.455 | 0.02112 | 21.5 | 4218 |
| mPEK-g-DND, 20 wt % | 20/80 | 21.5/78.5 | 1.79 | 0.400 | 0.04206 | 9.5 | 1864 |
| mPEK-g-DND, 30 wt % | 30/70 | 31.9/68.1 | 2.66 | 0.347 | .06251 | 5.6 | 1099 |

$^a$Theoretical calculation as followed:
$$\text{wt \% mPEK} = \frac{\text{wt \% PBA}/214.20 \text{ (FW } C_{13}H_{10}O_3) \times 196.20 \text{ (FW } C_{13}H_8O_2)}{\text{wt \% PBA}/214.20 \text{ (FW } C_{13}H_{10}O_3) \times 196.20 \text{ (FW } C_{13}H_8O_2) + \text{wt \% DND}}$$
wt % DND = 1 − wt % mPEK
$^b$For a 100 g sample, mol (DND) = wt (DND)/12.01 and mol(mPEK) = wt (mPEK)/196.20 (FW $C_{13}H_8O_2$).
$^c$Total number of grafting sites (mol): mol(DND) × 0.0235 based on the assumption that there are 2.35 arylcarbonylation sites for every 100 carbons of the DND.
$^d$Degree of polymerization (DP)/chain = mol(mPEK)/mol(grafting sites).
$^e$MW (mPEK) = DP × 196.20 (FW $C_{13}H_8O_2$).

We claim:

1. A poly(ether-ketone) composite of the formula:

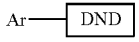

wherein DND is detonation nanodiamonds particle, wherein Ar represents ether-ketone repeating groups of the formula

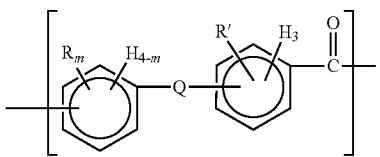

wherein Q is —O— or —O—$(CH_2)_n$—O—, wherein n has a value of 2-12; wherein R is —H, —$CH_3$, or —$C_2H_5$, m has a value of 1 or 2; wherein R' is —H or —$CH_3$; and wherein — denotes the presence of a direct C—C bond between Ar and DND.

2. The composite of claim 1 wherein Q is —O—, R is —H, m is 2 and R' is —H.

3. A process for preparing a poly(ether-ketone) composite of the formula

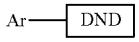

wherein Ar represents ether-ketone repeating groups of the formula

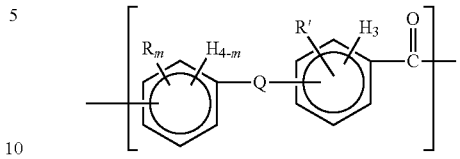

wherein Q is —O— or —O—$(CH_2)_n$—O—, wherein n has a value of 2-12; wherein R is —H, —$CH_3$— or —$C_2H_5$, m has a value of 1 or 2; wherein R is —H or —$CH_3$; and wherein — denotes the presence of a direct C—C bond between Ar and DND, which comprises the steps of (a) combining an aromatic acid of the formula

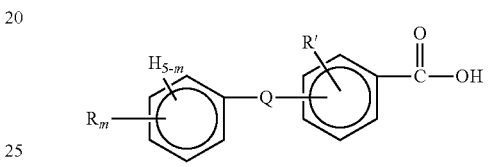

wherein R, R', m and Q are as described above, detonation nanodiamond particulates, and 83% PPA, (b) stirring this mixture at about 130° C. for about 3 hours, (c) adding additional $P_2O_5$ equivalent to 25 wt % of 83% PPA used leading to a total $P_2O_5$ content of about 86.7%, and (d) continuing to heat the mixture with stirring for about 24-60 hours, and (e) recovering the reaction product.

* * * * *